(12) United States Patent
Joshi

(10) Patent No.: US 9,435,830 B2
(45) Date of Patent: Sep. 6, 2016

(54) IMPLANTABLE MEDICAL DEVICE DEPTH ESTIMATION

(71) Applicant: CYBERONICS, INC., Houston, TX (US)

(72) Inventor: Himanshu Joshi, Houston, TX (US)

(73) Assignee: CYBERONICS, INC., Houston, TX (US)

(*) Notice: Subject to any disclaimer, the term of this patent is extended or adjusted under 35 U.S.C. 154(b) by 385 days.

(21) Appl. No.: 13/745,421

(22) Filed: Jan. 18, 2013

(65) Prior Publication Data

US 2014/0203823 A1    Jul. 24, 2014

(51) Int. Cl.
| | |
|---|---|
| *G01R 27/28* | (2006.01) |
| *G01R 19/00* | (2006.01) |
| *A61N 1/378* | (2006.01) |
| *A61N 1/372* | (2006.01) |

(52) U.S. Cl.
CPC ......... *G01R 19/0092* (2013.01); *A61N 1/3787* (2013.01); *A61N 1/37223* (2013.01)

(58) Field of Classification Search
USPC ....................................................... 324/655
See application file for complete search history.

(56) References Cited

U.S. PATENT DOCUMENTS

| | | |
|---|---|---|
| 4,702,254 A | 10/1987 | Zabara |
| 4,867,164 A | 9/1989 | Zabara |
| 4,979,511 A | 12/1990 | Terry, Jr. |
| 5,025,807 A | 6/1991 | Zabara |
| 5,154,172 A | 10/1992 | Terry et al. |
| 5,179,950 A | 1/1993 | Stanislaw |
| 5,186,170 A | 2/1993 | Varrichio et al. |
| 5,188,104 A | 2/1993 | Wernicke et al. |
| 5,205,285 A | 4/1993 | Baker, Jr. |
| 5,215,086 A | 6/1993 | Terry et al. |
| 5,215,089 A | 6/1993 | Baker, Jr. |
| 5,222,494 A | 6/1993 | Baker, Jr. |
| 5,231,988 A | 8/1993 | Wernicke et al. |
| 5,235,980 A | 8/1993 | Varrichio et al. |
| 5,263,480 A | 11/1993 | Wernicke et al. |
| 5,269,303 A | 12/1993 | Wernicke et al. |
| 5,299,569 A | 4/1994 | Wernicke et al. |
| 5,304,206 A | 4/1994 | Baker et al. |
| 5,330,515 A | 7/1994 | Rutecki et al. |
| 5,335,657 A | 8/1994 | Terry et al. |
| 5,540,730 A | 7/1996 | Terry et al. |
| 5,571,150 A | 11/1996 | Wernicke et al. |

(Continued)

FOREIGN PATENT DOCUMENTS

WO        00/66221 A1    11/2000

OTHER PUBLICATIONS

International Application No. PCT/US2014/010915, Invitation to Pay Additional Fees and, Where Applicable, Protest Fee, dated May 2, 2014, 4 pages.

(Continued)

*Primary Examiner* — Benjamin M Baldridge

(74) *Attorney, Agent, or Firm* — Foley & Lardner LLP

(57) ABSTRACT

A method includes applying a signal to a primary coil of an external charging device. The signal causes the primary coil to inductively couple to a secondary coil of an implantable medical device that is implanted within tissue of a patient. The method also includes measuring a current at the primary coil. The method further includes estimating a depth of the implantable medical device within the tissue of the patient based on the measured current.

20 Claims, 7 Drawing Sheets

(56) References Cited

U.S. PATENT DOCUMENTS

| | | |
|---|---|---|
| 5,700,282 A | 12/1997 | Zabara |
| 5,707,400 A | 1/1998 | Terry et al. |
| 5,928,272 A | 7/1999 | Adkins et al. |
| 6,027,456 A | 2/2000 | Feler et al. |
| 6,205,359 B1 | 3/2001 | Boveja |
| 6,208,902 B1 | 3/2001 | Boveja |
| 6,212,431 B1 * | 4/2001 | Hahn .................. A61N 1/3787 607/61 |
| 6,269,270 B1 | 7/2001 | Boveja |
| 6,319,241 B1 | 11/2001 | King et al. |
| 6,339,725 B1 | 1/2002 | Naritoku et al. |
| 6,341,236 B1 | 1/2002 | Osorio et al. |
| 6,356,788 B2 | 3/2002 | Boveja |
| 6,366,813 B1 | 4/2002 | DiLorenzo |
| 6,366,814 B1 | 4/2002 | Boveja |
| 6,427,086 B1 | 7/2002 | Fischell et al. |
| 6,447,443 B1 | 9/2002 | Keogh et al. |
| 6,449,512 B1 | 9/2002 | Boveja |
| 6,473,644 B1 | 10/2002 | Terry |
| 6,490,486 B1 | 12/2002 | Bradley |
| 6,505,074 B2 | 1/2003 | Boveja et al. |
| 6,556,868 B2 | 4/2003 | Naritoku et al. |
| 6,558,382 B2 | 5/2003 | Jahns et al. |
| 6,560,486 B1 | 5/2003 | Osorio et al. |
| 6,564,102 B1 | 5/2003 | Boveja |
| 6,610,713 B2 | 8/2003 | Tracey |
| 6,611,715 B1 | 8/2003 | Boveja |
| 6,615,081 B1 | 9/2003 | Boveja |
| 6,615,085 B1 | 9/2003 | Boveja |
| 6,668,191 B1 | 12/2003 | Boveja |
| 6,760,626 B1 | 7/2004 | Boveja |
| 6,768,969 B1 | 7/2004 | Nikitin et al. |
| 6,904,390 B2 | 6/2005 | Nikitin et al. |
| 6,920,357 B2 | 7/2005 | Osorio et al. |
| 7,043,305 B2 | 5/2006 | KenKnight et al. |
| 7,054,792 B2 | 5/2006 | Frei et al. |
| 7,130,695 B2 | 10/2006 | Czygan et al. |
| 7,171,271 B2 | 1/2007 | Koh et al. |
| 7,174,206 B2 | 2/2007 | Frei et al. |
| 7,174,216 B1 | 2/2007 | Dalal |
| 7,177,678 B1 | 2/2007 | Osorio et al. |
| 7,188,053 B2 | 3/2007 | Nikitin et al. |
| 7,204,833 B1 | 4/2007 | Osorio et al. |
| 7,321,837 B2 | 1/2008 | Osorio et al. |
| 7,324,850 B2 | 1/2008 | Persen et al. |
| 7,324,851 B1 | 1/2008 | DiLorenzo |
| 7,346,391 B1 | 3/2008 | Osorio et al. |
| 7,389,144 B1 | 6/2008 | Osorio et al. |
| 7,401,008 B2 | 7/2008 | Frei et al. |
| 2005/0075697 A1 * | 4/2005 | Olson .................. A61N 1/3787 607/61 |
| 2006/0016452 A1 * | 1/2006 | Goetz ...................... A61B 5/06 128/899 |
| 2007/0129767 A1 * | 6/2007 | Wahlstrand ....... A61M 5/14276 607/33 |
| 2007/0255318 A1 * | 11/2007 | Dudding ................ A61N 1/378 607/2 |
| 2009/0112291 A1 * | 4/2009 | Wahlstrand .......... A61N 1/3787 607/61 |
| 2010/0137948 A1 * | 6/2010 | Aghassian ........... A61N 1/3787 607/61 |
| 2010/0201316 A1 * | 8/2010 | Takada et al. ................. 320/108 |
| 2011/0101996 A1 * | 5/2011 | Potyrailo .............. G01D 21/00 324/655 |
| 2011/0241440 A1 * | 10/2011 | Sakoda et al. ................. 307/104 |
| 2012/0197322 A1 * | 8/2012 | Skelton et al. .................... 607/2 |
| 2012/0277829 A1 * | 11/2012 | Chow .................. A61N 1/3787 607/61 |
| 2012/0286807 A1 * | 11/2012 | Kolbi ..................... G01R 27/02 324/655 |
| 2013/0093436 A1 * | 4/2013 | Thorn .................... G01B 7/003 324/655 |
| 2013/0197613 A1 * | 8/2013 | Kelly et al. ..................... 607/96 |
| 2014/0015327 A1 * | 1/2014 | Keeling ................ B60L 11/182 307/104 |
| 2014/0024919 A1 * | 1/2014 | Metzenthen ......... H04B 5/0075 600/409 |
| 2014/0285029 A1 * | 9/2014 | Ichikawa .................. B60L 7/14 307/104 |

OTHER PUBLICATIONS

Harrison, Reid R., "Designing Efficient Inductive Power Links for Implantable Devices," Proc. 2007 IEEE Intl. Symposium on Circuits and Systems (ISCAS 2007), New Orleans, LA, pp. 2080-2083, 2007.

* cited by examiner

IMPLANTABLE MEDICAL DEVICE DEPTH ESTIMATION

FIELD OF THE DISCLOSURE

The present disclosure is generally related to implantable medical devices.

BACKGROUND

Advances in technology have led to the development of small medical devices that can be implanted within a living organism, such as a human, to provide treatment or monitoring. Powering such implantable medical devices may be challenging. An onboard battery of an implantable medical device may provide a limited amount of power due to a finite amount of energy that can be stored in the onboard battery. Replacing a battery of the implantable medical device may be expensive and inconvenient. For example, invasive surgery may be needed to replace the battery of the implantable medical device after it is implanted in a patient. Due to these and other concerns, some implantable medical devices may use rechargeable batteries.

However, charging a rechargeable battery of an implantable medical device may present other challenges. Charging inefficiencies may result in long charging times that may be undesirable for patients and may reduce compliance with a charging procedure. Such inefficiencies may be dependent on various factors that may be associated with use of a charging device to facilitate the charging. Some factors include alignment, position, and distance between the charging device and the implantable medical device.

SUMMARY

Charging inefficiencies of an implantable medical device may reduce compliance with a charging procedure, may lead to longer charging time, or both. Factors associated with such charging inefficiencies may also affect communication efficiency between the implantable medical device and an external device (e.g., an external charging device or an external programming device). Systems and methods described herein may improve charging efficiency of an implantable medical device, may improve communication efficiency between the implantable medical device and the external device, or may improve both charging efficiency and communication efficiency.

For example, information determined during charging of the implantable medical device may be used to adjust charging parameters (e.g., duty cycle of a charging signal, frequency of the charging signal, distance between a coil of a charging device and a coil of the implantable medical device, or other parameters) to improve charging efficiency of the implantable medical device. To illustrate, the distance between the coil of the charging device and the coil of the implantable medical device may be estimated based on a current applied to the coil of the charging device and other factors. The distance may provide an estimate of depth of the implantable medical device within tissue of the patient. Charging efficiency of the implantable medical device is related to the distance between the coil of the charging device and the coil of the implantable medical device, which is related to the depth of the implantable medical device within the tissue of the patient. Thus, for example, when the depth of the implantable medical device within the tissue of the patient less than a threshold depth, the distance between the coil of the charging device and the coil of the implantable medical device may be increased (e.g., by moving the charging device away from the implantable medical device) to improve charging efficiency.

In another example, the estimated depth of the implantable medical device within tissue of the patient may be used to pre-tune a tunable matching network to improve communication efficiency between the implantable medical device and an external device (e.g., the charging device, a programming device, or another device). The communication efficiency may be related to impedance matching of an antenna within the implantable medical device. The impedance matching may be related to the depth of the implantable medical device within the tissue of the patient, a type of tissue in which the implantable medical device is implanted, or both. Accordingly, the depth of the implantable medical device estimated during a charging period may be used (e.g., during the charging period) to set parameters for the tunable matching network. Thus, time and signaling that would be used during a communication period (e.g., following the charging period) to tune the tunable matching network may be avoided, thereby increasing communication efficiency.

In a particular embodiment, a method includes applying a signal to a primary coil of an external charging device. The signal causes the primary coil to inductively couple to a secondary coil of an implantable medical device that is implanted within tissue of a patient. The method also includes measuring a current at the primary coil. The method further includes estimating a depth of the implantable medical device within the tissue of the patient based on the measured current.

In another particular embodiment, a device includes a primary coil configured to inductively couple to a secondary coil of an implantable medical device. The device also includes a current measurement device coupled to the primary coil and configured to measure a current applied to the primary coil while the secondary coil is inductively coupled to the primary coil. The device further includes a processor coupled to the current measurement device. The processor is configured to estimate a depth of the implantable medical device within tissue of a patient based on the measured current.

In another particular embodiment, a method includes inductively coupling a secondary coil of an implantable medical device that is implanted within tissue of a patient to a primary coil of an external charging device. The method also includes receiving data from an external device. The data is indicative of an estimated depth of the implantable medical device within the tissue of the patient. The estimated depth is determined based on a current measured at the external charging device while the secondary coil is inductively coupled to the primary coil.

In another particular embodiment, an implantable medical device includes a secondary coil configured to inductively couple to a primary coil of an external charging device. The implantable medical device also includes a receiver configured to receive data from an external device. The received data is indicative of an estimated depth of the implantable medical device within tissue of a patient. The estimated depth is determined based on a current measured at the external charging device while the secondary coil is inductively coupled to the primary coil. The implantable medical device further includes a matching network that is adjustable based on the received data.

DETAILED DESCRIPTION

Figure 1:
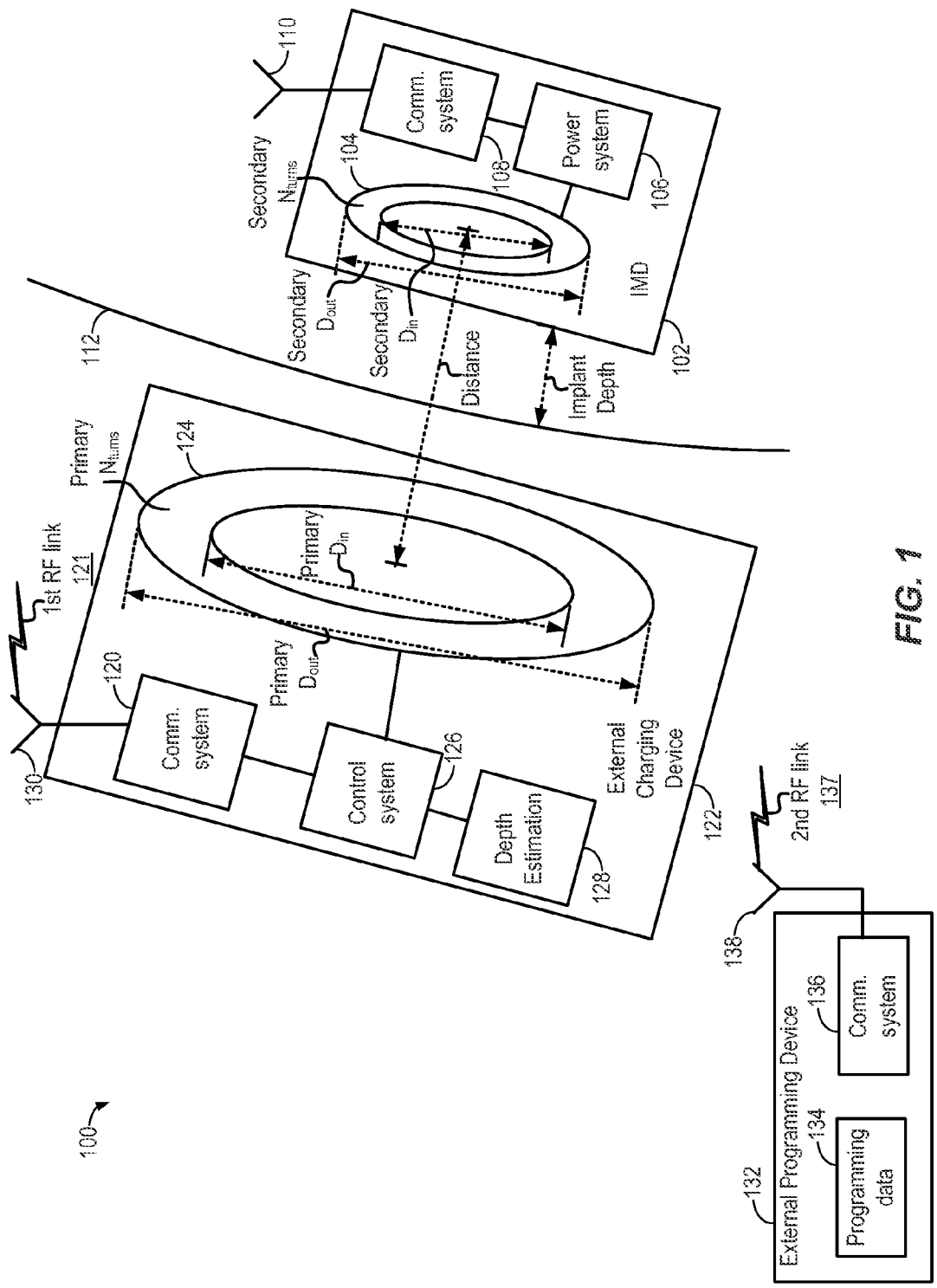
FIG. 1 is a block diagram of a first particular embodiment of a system to estimate a depth of an implantable medical device during charging of the implantable medical device.

FIG. 1 is a block diagram of a first particular embodiment of a system 100 to estimate a depth of an implantable medical device 102 within tissue of a patient 112 during charging of the implantable medical device 102. For example, the implantable medical device 102 may be charged by an external charging device 122 via inductive coupling of a primary coil 124 of the external charging device 122 and a secondary coil 104 of the implantable medical device 102. Current induced at the secondary coil 104 may be rectified and applied to a battery of a power system 106 of the implantable medical device 102.

In a particular embodiment, the implantable medical device 102 includes a communication system 108. The communication system 108 may include one or more antennas, such as an antenna 110. The communication system 108 may be used to send information from the implantable medical device 102 via the antenna 110 and/or to receive information at the implantable medical device 102 via the antenna 110. To illustrate, during a charging period (e.g., while the implantable medical device 102 is being charged by the external charging device 122), the communication system 108 may send information related to charging of the implantable medical device 102 to the external charging device 122 to facilitate the charging process. Examples of information that may be sent to the external charging device 122 include a state of the battery of the implantable medical device 102 (e.g., a charge level of the battery, a charging rate of the battery, a voltage applied to the battery based on the current induced at the secondary coil 104), settings information (e.g., therapy settings, data gathering settings, charging settings or communication settings), other data, or a combination thereof.

The communication system 108 may also be used to send and/or receive information during a programming period. The programming period may be subsequent to the charging period, before the charging period or interleaved with the charging period. For example, after the battery of the implantable medical device 102 is charged, an external programming device 132 may be used to transmit programming data 134 to the implantable medical device 102. In another example, the external programming device 132 may transmit the programming data 134 to the implantable medical device 102 before the charging period. In yet another example, the charging period may be interrupted (e.g., charging of the battery may be stopped temporarily), during the programming period, to transmit the programming data 134.

In a particular embodiment, the external charging device 122 includes or utilizes a first communication system 120 to communicate with the implantable medical device 102, and the external programming device 132 includes or utilizes a second communication system 136 to communicate with the implantable medical device 102. The first communication system 120 may communicate with the implantable medical device 102 via a first radio frequency (RF) link 121, and the second communication system 136 may communicate with the implantable medical device 102 via a second RF link 137. As an example, the first RF link 121 may be used during the charging period to provide charging feedback from the implantable medical device 102 to the external charging device 122. The second RF link 137 may be used during the programming period to send the programming data 134 from the external programming device 132 to the implantable medical device 102. In this example, since the first RF link 121 is used during the charging period, power used to support the first RF link 121 is not a significant concern. The power is not a drain on the battery of the implantable medical device 102 because external power is being provided to the implantable medical device 102. However, power utilized to support the second RF link 137 during the programming period is provided by the battery of the implantable medical device 102, and therefore decreases power available for other functions of the implantable medical device 102, such as providing therapy to the patient 112.

Additionally, in some embodiments, signals used by the first RF link 121 and signals used by the second RF link 137 may be different. For example, the first RF link 121 may use near-field signals, e.g., relatively short range electromagnetic signals, and the second RF link 137 may use far-field signals, e.g., longer range electromagnetic signals. Impedance of tissue of the patient 112 in which the implantable medical device 102 is implanted may affect the far-field signals of the second RF link 137 more strongly than the impedance affects the near-field signals of the first RF link 121. In a particular embodiment, the communication system 108 of the implantable medical device 102 may be designed for use at a particular implant depth (e.g., one inch) and for implantation within a particular type of tissue (e.g., fat). When the implantable medical device 102 is at a depth that is different than the design depth (e.g., due to where the implantable medical device 102 was implanted, due to shifting of the implantable medical device 102 after implantation or due to growth of scar tissue over the implantable medical device 102 after implantation), or when the implantable medical device 102 is implanted in tissue other than the design tissue type (e.g., implanted in muscle rather than fat), an impedance mismatch may occur at the implantable medical device 102, degrading reception of signals transmitted via the second RF link 137. The communication system 108 may include a tunable matching network (not shown in FIG. 1) that is adjustable to improve impedance matching and to improve communication efficiency via the second RF link 137.

In a particular embodiment, the communication system 108 may tune the tunable matching network before the programming period (e.g., before the second RF link 137 is established) based on information determined during the charging period. Thus, the tunable matching network may be tuned to improve performance of the second RF link 137 before the second RF link 137 is established. For example, the external charging device 122 may estimate the implant depth of the implantable medical device 102 during the charging period. The external charging device 122 may send information related to the implant depth to the implantable medical device 102 via the first RF link 121. The information sent to the implantable medical device 102 may include a value indicating the implant depth, settings for the tunable matching network (e.g., tuning parameters of the tunable matching network) of the implantable medical device 102 that are determined based on the implant depth, or both. The information related to the implant depth to the implantable medical device 102 may be used by the communication system 108 to tune the matching network in preparation for establishment of the second RF link 137.

In a particular embodiment, the system 100 may be designed to charge the implantable medical device 102 at a particular implant depth. For example, a size of the primary coil 124 (e.g., an external diameter, Primary $D_{out}$, an internal diameter, Primary $D_{in}$, or a number of turns, Primary $N_{turns}$) may be selected to enable the external charging device 122 to charge the implantable medical device 102 efficiently. As another example, a size of the secondary coil 104 (e.g., an external diameter, Secondary $D_{out}$, an internal diameter, Secondary $D_{in}$, or a number of turns, Secondary $N_{turns}$) may be selected to enable the external charging device 122 to charge the implantable medical device 102 efficiently. In this embodiment, when the primary coil 124 is too far from or too close to the secondary coil 104, charging efficiency may be reduced, which may lead to increased heating of the implantable medical device 102 due to resistive losses, increased charging times, or both.

In a particular embodiment, the estimated implant depth of the implantable medical device 102 determined by the external charging device 122 may be used to improve charging efficiency. For example, when the implant depth indicates that the implantable medical device 102 is too shallow (i.e., a distance between the secondary coil 104 and the primary coil 124 is too small), the external charging device 122 may be moved away from the patient 112 in order to increase the distance between the secondary coil 104 and the primary coil 124. When the implant depth indicates that the implantable medical device 102 is too deep (i.e., the distance between the secondary coil 104 and the primary coil 124 is too large), a control system 126 of the external charging device 122 may provide an operator of the external charging device 122 with an indication that the charging period may be extended (e.g., to reduce resistive heating of the implantable medical device 102 due to inefficient charging).

In a particular embodiment, the external charging device 122 may include a depth estimation system 128. The depth estimation system 128 may be configured to estimate the implant depth of the implantable medical device 102 during the charging period. For example, the depth estimation system 128 may receive information (e.g., from the control system 126 or by direct measurement) indicating current applied to the primary coil 124 during the charging period. When a charging signal applied by the control system 126 to the primary coil 124 is at a resonant frequency of an inductively coupled system including the primary coil 124 (and its driving circuit) and the secondary coil 104 (and its load circuit), the current through to the primary coil 124 (e.g., a root-mean square (RMS) current of the charging signal), $I_{primary}$, may be a function of resistance of the primary coil 124 and its driving circuit, $R_{primary}$, a reflected resistance associated with the inductively coupled system, $R_{reflected}$, and a voltage induced at the secondary coil 104, $V_{induced}$. The relationship of $I_{primary}$ to $R_{primary}$, $R_{reflected}$, and $V_{induced}$ may be approximated by the equation:

$$I_{primary}=V_{induced}/(R_{primary}+R_{reflected})$$

The voltage induced at the secondary coil 104, $V_{induced}$, may be measured by the power system 106 and transmitted to the external charging device 122 via the first RF link 121. The resistance of the primary coil 124 and its driving circuit, $R_{primary}$, may be predetermined (e.g., via a calibration process) and stored at a memory of the depth estimation system 128, the control system 126 or another component of the external charging device 122. A coupling coefficient, k, of the inductively coupled system is a function of the distance between the primary coil 124 and the secondary coil 104. The reflected resistance associated with the inductively coupled system, $R_{reflected}$, may be proportional to a second power of the coupling coefficient of the system, $k^2$. Thus, the reflected resistance, $R_{reflected}$, may be a strong function of the distance, and changes in the reflected resistance, $R_{reflected}$, may be detected by measuring the current through to the primary coil 124, $I_{primary}$. Thus, the distance between the primary coil 124 and the secondary coil 104 can be estimated based on the measured current through to the primary coil 124, $I_{primary}$. The implant depth can be estimated based on the estimated distance and physical configuration information (e.g., known dimensions) of the external charging device 122 and the implantable medical device 102.

In a particular embodiment, the depth estimation system 128 may include a look-up table, another data structure, an algorithm or other logic that relates measured values of the current through to the primary coil 124, $I_{primary}$, to implant depths. Thus, the external charging device 122 may estimate the implant depth of the implantable medical device 102 during a charging period.

In a particular embodiment, after the external charging device 122 estimates the implant depth, the external charging device 122 may send information related to the implant depth to the implantable medical device 102 via the first RF link 121. The communication system 108 of the implantable medical device 102 may adjust settings of the tunable matching network based on the information related to the implant depth. In a particular embodiment, after the second RF link 137 is established, the communication system 108 may further adjust the settings of the tunable matching network if needed to improve impedance matching associated with the second RF link 137. When the settings of the tunable matching network are adjusted further after the second RF link 137 is established, this may be an indication that the implantable medical device 102 is implanted in an unexpected tissue type. For example, the implantable medical device 102 may be implanted in muscle rather than fat. Since muscle and fat have different impedance values and since the settings of the tunable matching network may be pre-set based on the implant depth and based on an expectation that the implantable medical device 102 is implanted in fat, implantation of the implantable medical device 102 in muscle may cause an impedance mismatch. The implantable medical device 102 may send information to the external charging device 122 via the first RF link 121 or to the external programming device 132 via the second RF link 137 to indicate that the settings of the tunable matching network were further adjusted. The external charging device 122, the external programming device 132, or both, may store information in a memory regarding the estimated implant depth, the type of tissue in which the implantable medical device 102 is implanted, or both. During a later charging or programming period, the information may be retrieved from the memory for use as an initial estimate of implant depth or to compare to a current estimate of implant depth to identify changes (which may indicate movement of the implantable medical device 102). Current or historic estimates of implant depth or the tissue type may be provided as output to an operator to facilitate decision-making regarding treatment provided to the patient 112.

Thus, the system 100 may improve charging efficiency of the implantable medical device 102, may improve communication efficiency between the implantable medical device 102 and an external device (e.g., the external charging device 122 or the external programming device 132), or may improve both charging efficiency and communication efficiency.

Figure 2:
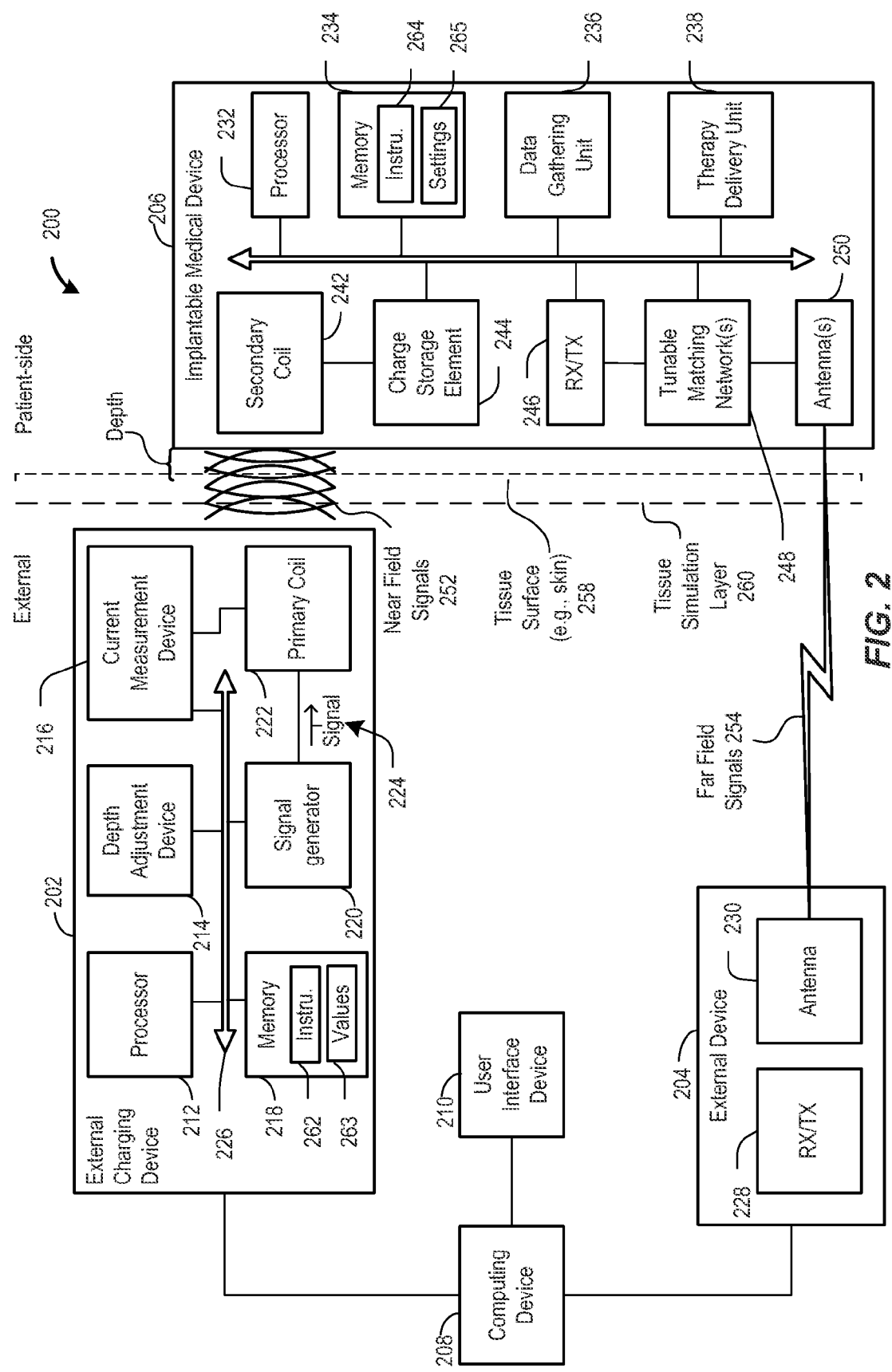
FIG. 2 is a block diagram of a second particular embodiment of a system to estimate a depth of an implantable medical device during charging of the implantable medical device.

FIG. 2 is a block diagram of a second particular embodiment of a system 200 to estimate a depth of an implantable medical device 206 during charging of the implantable medical device 206. The system 200 may include an external charging device 202, an external programming device 204, and an implantable medical device (IMD) 206. The external charging device 202 may include, be included within or correspond to the external charging device 122 of FIG. 1. The implantable medical device 206 may include, be included within or correspond to the implantable medical device 102 of FIG. 1. The external programming device 204 may include, be included within or correspond to the external programming device 132 of FIG. 1.

The external charging device 202 may be configured to supply power to the implantable medical device 206 to charge a charge storage element 244 (e.g., a battery or a capacitor) of the implantable medical device 206 via inductive coupling of a primary coil 222 of the external charging device 202 and a secondary coil 242 of the implantable medical device 206. For example, a signal generator 220 of the external charging device 202 may apply a signal 224 to the primary coil 222. The signal 224 may cause the primary coil 222 to inductively couple to the secondary coil 242 via near-field signals 252. The signal 224 may induce current flow at the secondary coil 242, which may be supplied to the charge storage element 244.

The external programming device 204 may be configured to communicate (e.g., to exchange data) with the implantable medical device 206 wirelessly. For example, the external programming device 204 may communicate with the implantable medical device 206 via far-field signals 254. In a particular embodiment, the external charging device 202 and the external programming device 204 may be coupled to or may communicate with a computing device 208 (e.g., a computer). The computing device 208 may receive programming instructions from an operator via a user interface device 210 (e.g., a keyboard, a mouse, a touch screen, etc.).

The implantable medical device 206 may be surgically implanted in a patient to provide therapy, to monitor one or more conditions, for another purpose, or any combination thereof. In a particular embodiment, the implantable medical device 206 may be coupled to one or more electrodes (not shown) and may be adapted to deliver electrical stimulus to tissues of the patient via the electrodes. For example, the implantable medical device 206 may be a nerve stimulation device.

The external charging device 202 may include a processor 212 (e.g., a digital signal processor), a depth adjustment device 214, a current measurement device 216, a memory 218, a signal generator 220, and the primary coil 222. One or more of the processor 212, the depth adjustment device 214, the current measurement device 216, the memory 218, and the signal generator 220 may be coupled to each other via a system bus 226. One or more of the depth adjustment device 214, the current measurement device 216, or the signal generator 220 may be an electrical circuit, a stand-alone electronic device, or a combination thereof. The processor 212 may be configured to control the depth adjustment device 214, the current measurement device 216, the signal generator 220, the primary coil 222, or a combination thereof, responsive to processor executable instructions 262 stored in the memory 218.

The current measurement device 216 may be configured to measure a current at the primary coil 222. For example, the current measurement device 216 may measure $I_{primary}$, as described with reference to FIG. 1. The current measurement device 216 may store a value indicating the measured current at the memory 218, may provide the value to the processor 212, or both. The processor 212 may estimate the depth of the implant depth of the implantable medical device 206 within tissue of a patient based on the measured current. For example, the processor 212 may look up an estimated depth value in a lookup table in the memory 218 based on the current at the primary coil 222, information received from the implantable medical device 206, information descriptive of the signal 224, or a combination thereof.

The external programming device 204 may include a transmitter, a receiver, or a combination thereof (e.g., a transceiver 228) and an antenna 230. The transceiver 228 may be configured to communicate (e.g., transmit data, receive data, or a combination thereof) via the antenna 230 with the implantable medical device 206. For example, the external programming device 204 may send program data, such as therapy parameter data to the implantable medical device 206 using the far-field signals 254. The program data may be stored at a memory (not shown) of the external programming device 204, may be received from the computing device 208, or both.

The implantable medical device 206 may be powered internally by a power system that includes the charge storage element 244 (e.g., a battery, a power supply, etc.), which is recharged via the secondary coil 242. The implantable medical device 206 may also include a communication system, such as a transceiver 246, a tunable matching network 248, an antenna 250 or a combination thereof. The implantable medical device 206 may further include therapy or medical systems, such as a data gathering unit 236, a therapy delivery unit 238, or a combination thereof. The implantable medical device 206 may also include a control system that controls functions of other portions of the implantable medical device 206. For example, the control system may include a processor 232 and a memory 234 accessible to the processor 232. The memory 234 may store data and instructions 264 that are executable by the processor 232 to control the other portions of the implantable medical device 206. For example, the instructions 264 may include program data indicating therapy delivery parameters. The memory 234 may store settings data 265 indicating settings associated with operation of the implantable medical device 206. For example, the settings data 265 may include matching network settings or implant depth information received from the external charging device 202 based on the implant depth estimated by the external charging device 202.

The data gathering unit 236 may be configured to gather data related to an operational state of the implantable medical device 206 (e.g., a charge state of the charge storage element 244), data related to therapy provided to a patient, body parameter data corresponding to one or more body parameters of a patient, or a combination thereof. Data gathered by the data gathering unit 236 may be used to control therapy provided to the patient, may be transmitted to an external device, or both.

The therapy delivery unit 238 may be configured to provide therapy to the patient. For example, the therapy delivery unit 238 may provide electrical stimulation (via one or more electrodes (not shown) to tissue of the patient). As another example, the therapy delivery unit 238 may include a drug pump that delivers a drug or drugs to the patient. Therapy provided by the therapy delivery unit 238 may be controlled by the processor 232 based on a treatment program.

The tunable matching network 248 may be configured to control impedance matching of the antenna 250 and other components of the implantable medical device 206. For example, the tunable matching network 248 may include one or more variable capacitors that can be adjusted to reduce impedance mismatch associated with the antenna 250. The tunable matching network 248 may be adjusted based on settings 265 stored in the memory 234, based on settings received from the external charging device 202, or both. Additionally, after the tunable matching network 248 is adjusted, values indicating settings of the tunable matching network 248 may be stored in the memory 234. Information indicating the settings 265 of the tunable matching network 248 may be provided to the external charging device 202, to the external programming device 204, or both, to facilitate a determination of a type of tissue in which the implantable medical device 206 is implanted (as described with reference to FIG. 1).

During operation, after the implantable medical device 206 is implanted within tissues of a patient, the external charging device 202 may be used, during a charging period, to supply electrical power to the implantable medical device 206 to charge the charge storage element 244. In a particular embodiment, the external charging device 202 supplies electrical power to the implantable medical device 206 using the near-field signals 252. The external charging device 202 may also communicate with the implantable medical device 206 via the near-field signals 252 or other signals. For example, the external charging device 202 may send implant depth information to the implantable medical device 206. The implantable medical device 206 may use the implant depth information to pre-adjust the tunable matching network 248 for communication with the external device programming 204. The external charging device 202 may store a value 263 associated with the implant depth at the memory 218, may provide the implant depth information to the computing device 208, or both. The implant depth may be used during subsequent charging periods as an initial estimate of the implant depth or to determine whether the implant depth has changed.

The computing device 208 may provide an indication of the implant depth to an operator via the user interface device 210. When the implant depth is too deep (e.g., deeper than expected or deeper than a threshold depth), the operator may be notified that the charging period may be extended. When the implant depth is too shallow (e.g., shallower than expected or shallower than a threshold depth), the operator may be advised to increase the distance between the external charging device 202 and the implantable medical device 206. For example, the operator may apply a tissue simulation layer 260 to a tissue surface 258 (e.g., skin) of the patient. In a particular embodiment, the tissue simulation layer 260 may have impedance properties similar to tissue of the patient. Thus, the tissue simulation layer 260 may also facilitate impedance matching for communication between the implantable medical device 206 and the external programming device 204.

In a particular embodiment, the external charging device 202 may perform a frequency sweep to determine or estimate a charging frequency (e.g., a resonant frequency) of the inductive system. For example, the external charging device 202 may apply multiple charging signals 224 to the primary coil 222 to cause the primary coil 222 to inductively couple to the secondary coil 242. Each of the multiple charging signals 224 may be applied at a corresponding charging frequency and a corresponding duty cycle to cause a corresponding primary current to be generated across the primary coil 222.

The current measurement device 216 may measure the primary current, $I_{primary}$, as each signal is applied during the frequency sweep. The current measurement device 216 may store values 263 of the primary currents, the corresponding frequencies, and the duty cycles in the memory 218. The resonant frequency may be determined based on the values 263. For example, a primary current at the resonant frequency may have a lower value than primary currents at frequencies other than the resonant frequency for the same amount of power delivered to the implantable medical device 206.

The external charging device 202 may estimate a distance between the external charging device 202 and the implantable medical device 206 based on information received from the implantable medical device 206 and the measured primary current. In a particular embodiment, the distance is estimated further based on a dimension of the primary coil 222, a dimension of the secondary coil 242, or a combination thereof (as described with reference to FIG. 1). For example, the external charging device 202 may compare the measured primary current at the resonant frequency and an induced voltage at the secondary coil 242 of the implantable medical device 206 to values in a look up table to estimate the implant depth.

The processor 212 may compare the estimated implant depth to a threshold depth. The threshold depth may correspond to a designed implant depth of the implantable medical device 206. In a particular embodiment, the threshold depth corresponds to an implant depth that enables the external charging device 202 to supply electrical power to the implantable medical device 206 with a reduced or minimum duty cycle. When the estimated implant depth is greater than the threshold depth, the external charging device 202 may transmit a notification signal to the computing device 208 to notify the operator that a charging cycle may be extended to reduce overheating. For example, each charging period of a particular charging cycle may be reduced while a number of charging periods within the particular charging cycle may be increased. When the estimated implant depth is less than the threshold depth, the external charging device 202 may actuate the depth adjustment device 214 to increase the distance between the primary coil 222 and the secondary coil 242. In a particular embodiment, the depth adjustment device 214 may include an apparatus that is movable to adjust a distance between the primary coil and the secondary coil, such as a sliding mechanism (e.g., a linear motor).

Alternatively, or in addition, when the estimated implant depth is less than the threshold depth, the external charging device 202 may transmit a notification signal to the computing device 208 to notify the operator (e.g., via the user interface device 210) to apply the tissue simulation layer 260 (or some other type of layer or spacer) to the tissue surface 258. Applying the tissue simulation layer 260 to the tissue surface 258 may increase a distance between the primary coil 222 and the secondary coil 242 to enhance charging of the charge storage element 244. The tissue simulation layer 260 may have impedance that is substantially similar to impedance of human tissue. Also, the tissue simulation layer 260 may have a particular thickness such that a sum of the particular thickness and the estimated implant depth substantially matches the threshold depth.

In a particular embodiment, after adjusting the distance between the primary coil 222 and the secondary coil 242, the external charging device 202 continues to receive the voltage information of the charge storage element 244 from the implantable medical device 206. Based on the received voltage information, the external charging device 202 may adjust a duty cycle and/or a frequency of the signal 224 to facilitate charging of the charge storage element 244. For example, a voltage applied to the charge storage element 244 may increase as the charge state of the charge storage element 244 increases. The duty cycle and/or the frequency of the signal 224 may be adjusted for efficient charging based on the voltage applied to the charge storage element 244.

In a particular embodiment, the external charging device 202 may determine settings or other implantable medical device operational parameters based on the estimated implant depth. The settings may be determined based on simulations, based on information stored in the memory 218, or both. For example, the settings may correspond to values of impedance matching capacitors in the tunable matching network 248. The external charging device 202 may transmit the determined settings as settings data to the implantable medical device 206. In a particular embodiment, the external charging device 202 may transmit the estimated implant depth as depth data to the implantable medical device 206. The processor 232 and/or the tunable matching network 248 may determine one or more settings (e.g., one or more matching network parameter values) of the tunable matching network 248 based on the depth data and adjust the tunable matching network 248 based on the determined settings.

Thus, instead of, or in addition to, adjusting the tunable matching network 248 during a programming period, which may consume electrical power from the charge storage element 244 and reduce time available for communication with the external programming device 204, the configuration of the tunable matching network 248 may be adjusted during the charging period. After the charging period is over, the implantable medical device 206 may communicate with the external programming device 204 during a programming period or a communication period. The implantable medical device 206 may transmit one or more therapy delivery parameters, body parameter data, status data, etc., to the external programming device 204 during the communication period. Alternatively, or in addition, the external programming device 204 may transmit one or more therapy delivery parameters to the implantable medical device 206 during the communication period.

In a particular embodiment, the processor 212 may calculate an average value of primary currents measured, during a charging period, or during a portion of the charging period (e.g., during a constant current portion of the charging period), to estimate misalignment between the primary coil 222 and the secondary coil 242. For example, the misalignment may be caused by patient motion during the constant current portion of the charging period. A lowest value of the primary current during the charging period may be used to estimate the implant depth.

Figure 3:
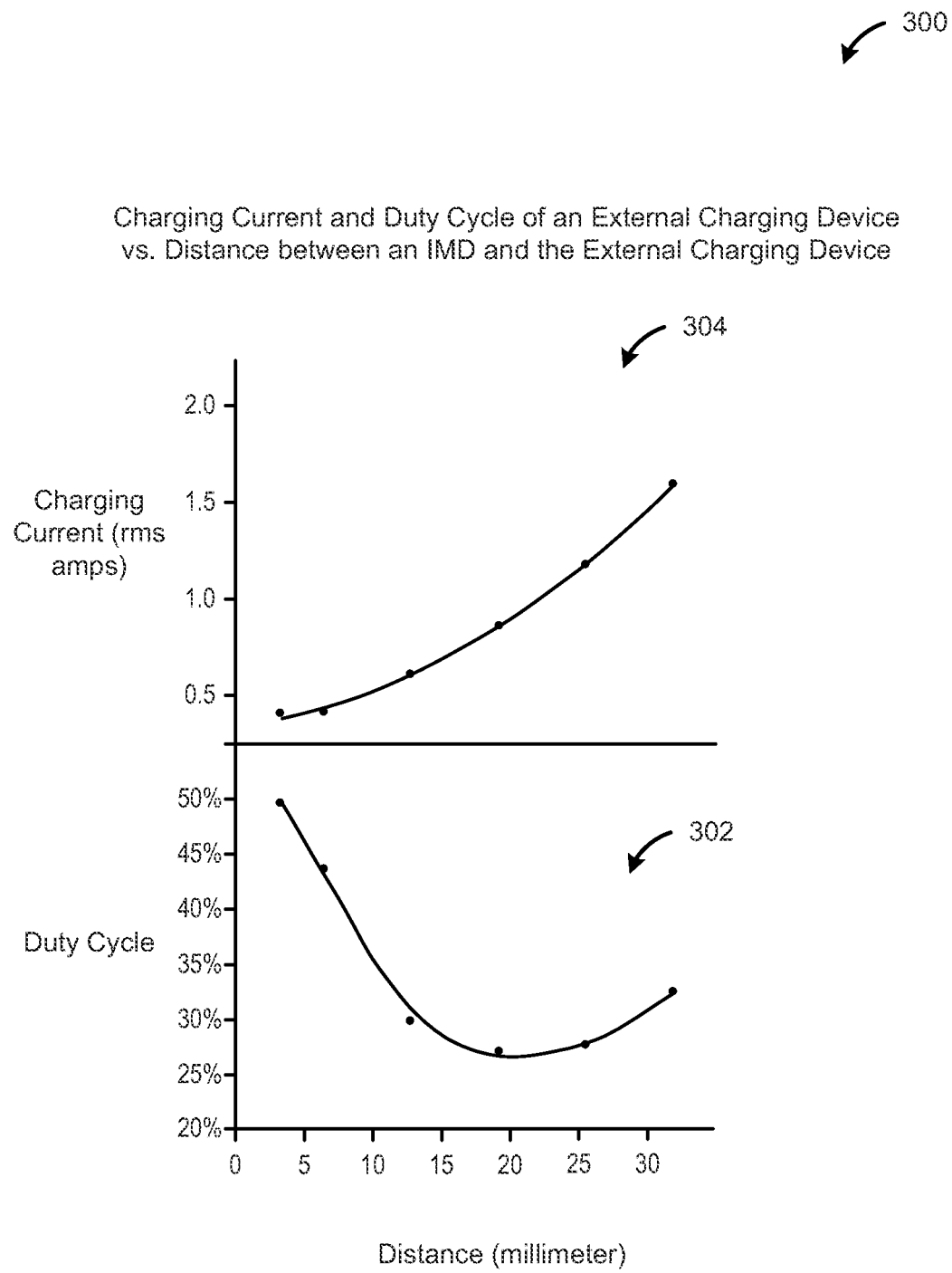
FIG. 3 is a diagram illustrating a relationship between charging current and duty cycle of an external charging device.

Referring to FIG. 3, a diagram 300 illustrating a relationship between a current at a primary coil of an external charging device (such as the external charging device 122 of FIG. 1 or the external charging device 202 of FIG. 2), duty cycles of the external charging device, and implant depths of the implantable medical device 206 is shown according to an exemplary embodiment. The diagram 300 includes a duty cycle curve 302 illustrating changes in duty cycle to achieve a particular charging voltage (e.g., $V_{induced}$ as described with reference to FIG. 1) at an implantable medical device based on depth of the implantable medical device. The duty cycle curve 302 illustrates that a minimum duty cycle is achieved at a particular implant depth.

The diagram 300 also includes a charging current curve 304 illustrating changes in the primary current to achieve a particular charging voltage (e.g., $V_{induced}$ as described with reference to FIG. 1) at an implantable medical device based on depth of the implantable medical device. The charging current curve 304 illustrates that the primary current increases as the implant depth increases.

Figure 4:
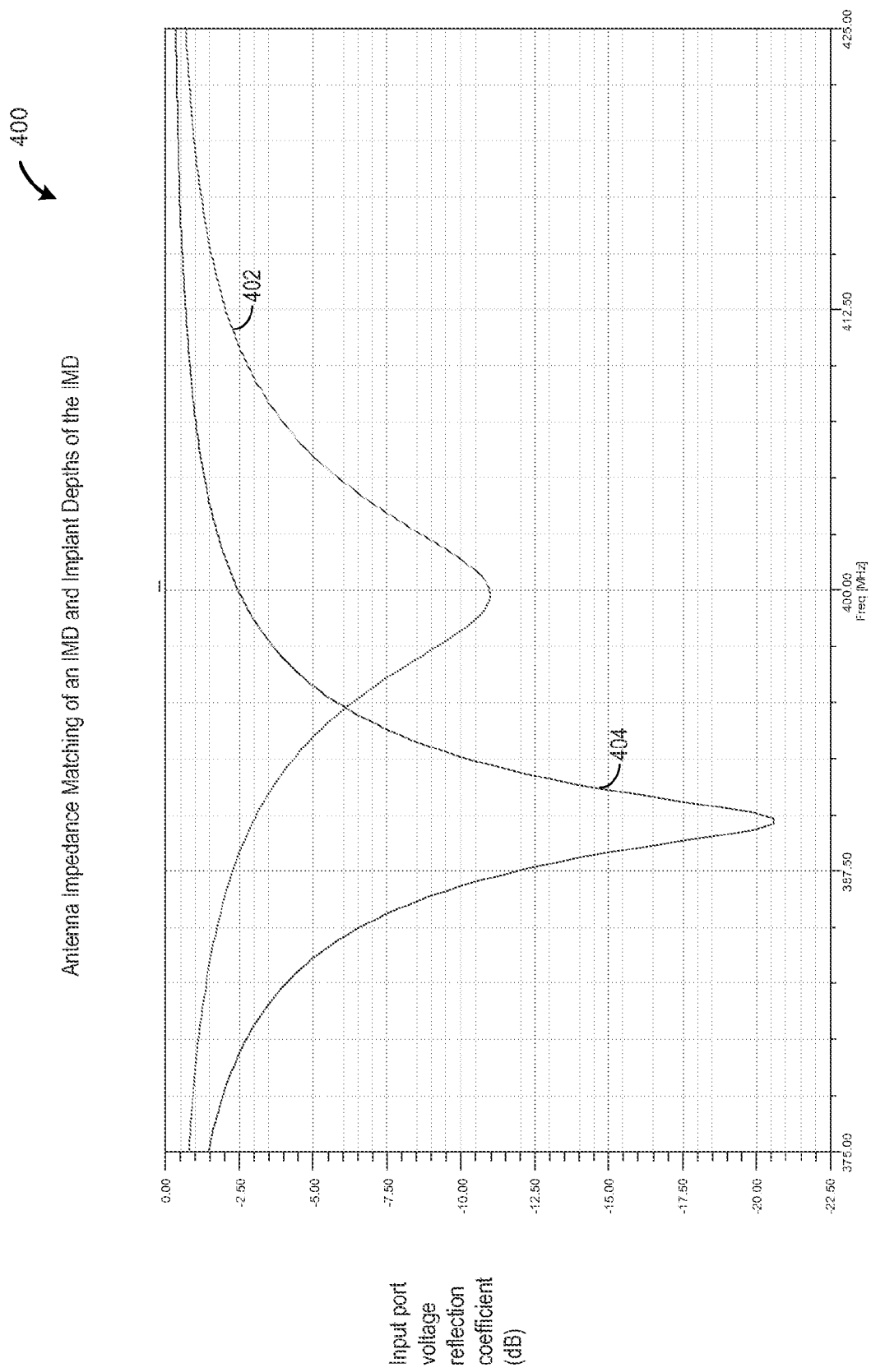
FIG. 4 is a diagram illustrating a relationship between implant depths of the implantable medical device and corresponding antenna matching for an antenna of the implantable medical device.

Referring to FIG. 4, a diagram 400 illustrating a relationship between implant depths of the implantable medical device 206 of FIG. 2 and corresponding impedance matching for the antenna 250 is shown according to an exemplary embodiment. The diagram 400 may include a first impedance matching curve 402 and a second impedance matching curve 404. The first impedance matching curve 402 is based on an implant depth that corresponds to a design implant depth (e.g., one (1) inch in this example). The second impedance matching curve 404 is based on an implant depth that is less than the design implant depth (e.g., about one half (½) inch). As the diagram 400 illustrates, a frequency corresponding to a best impedance match at the design depth is different than a frequency that corresponds to the best impedance match at less than the design depth. Thus, a matching network of an implantable medical device may be adjusted for improved performance based on the implant depth, as described with reference to FIGS. 1 and 2. Alternatively, or in addition, a spacer (e.g., the tissue simulation layer 260 of FIG. 2) may be used to compensate for the difference between the first implant depth and the second implant depth (when the second implant depth is less than the first implant depth) to improve impedance matching.

Figure 5:
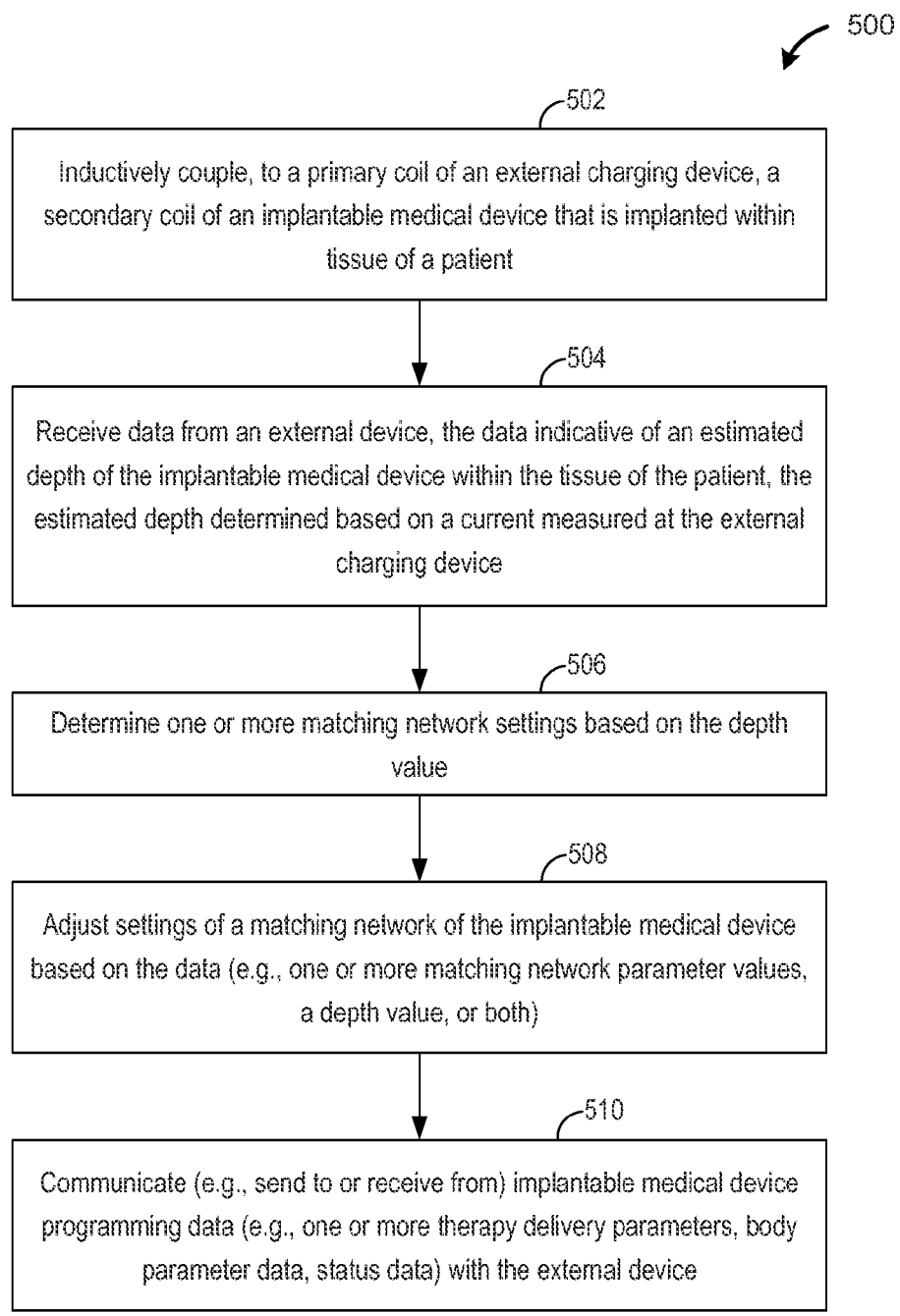
FIG. 5 is a flow chart of a first particular embodiment of a method of operation an implantable medical device.

Referring to FIG. 5, a flow chart of a particular embodiment of a method 500 of operation of an implantable medical device, such as the implantable medical device 102 of FIG. 1 or the implantable medical device 206 of FIG. 2. The method 500 includes inductively coupling, to a primary coil of an external charging device, a secondary coil of the implantable medical device that is implanted within tissue of a patient, at 502. For example, referring to FIG. 2, the primary coil 222 of the external charging device 202 may be inductively coupled to the secondary coil 242 of the implantable medical device 206.

The method 500 also includes receiving data from an external device, at 504. The data may be indicative of an estimated depth of the implantable medical device within the tissue of the patient. The estimated depth is determined based on a current measured at the external charging device. For example, referring to FIG. 2, based on received voltage information and a measured primary current, the external charging device 202 may estimate a distance between the external charging device 202 and the implantable medical device 206. The external charging device 202 may transmit the estimated distance as depth data to the implantable medical device 206.

Figure 6:
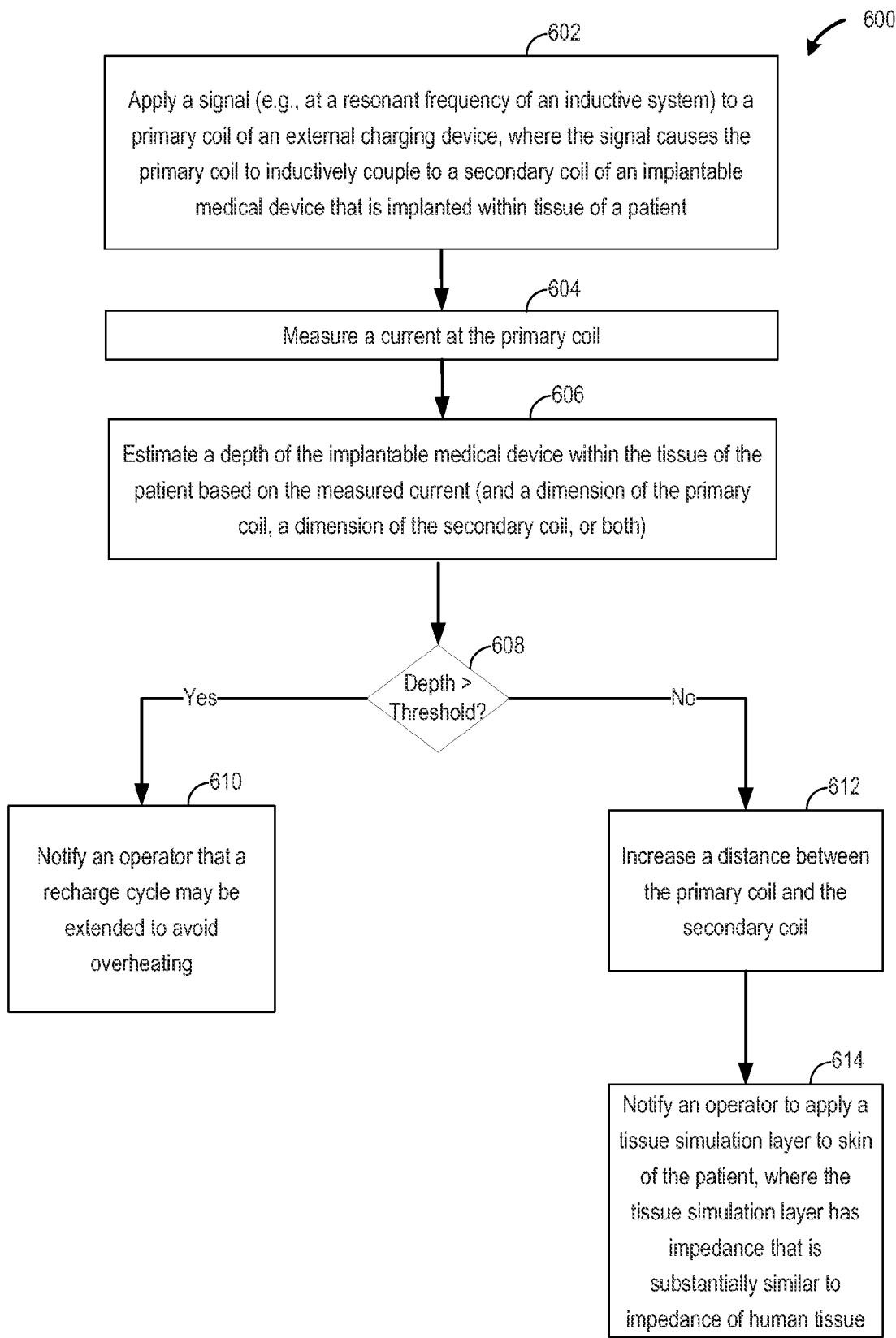
FIG. 6 is a flow chart of a first particular embodiment of a method of operation of an external charging device.

The method 500 further includes determining one or more matching network settings based on the depth value, at 506. For example, referring to FIG. 2, the processor 232 and/or the tunable matching network 248 may determine one or more settings (e.g., one or more matching network parameter values for the tunable matching network 248 based on the depth data. The method 500 further includes adjusting settings of the matching network of the implantable medical device based on the data (e.g., one or more matching network parameter values, a depth value, or both), at 508. For example, referring to FIG. 2, the processor 232 and/or the tunable matching network 248 may adjust the tunable matching network 248 based on the determined settings. The method 500 further includes communicating (e.g., send to or receive from) implantable medical device programming data (e.g., one or more therapy delivery parameters, body parameter data, status data) with the external device, at 510. For example, referring to FIG. 2, the implantable medical device 206 may transmit one or more therapy delivery parameters, body parameter data, status data, etc., to the external programming device 204 during a communication period. As another example, the external programming device 204 may transmit one or more therapy delivery parameters to the implantable medical device 206 during the communication period Referring to FIG. 6, a flow chart of a first particular embodiment of a method 600 of operation of an external charging device, such as the external charging device 122 of FIG. 1 or the external charging device 202 of FIG. 2. The method 600 includes applying a signal (e.g., at a resonant frequency of an inductive system) to a primary coil of the external charging device, at 602. The signal may cause the primary coil to inductively couple to a secondary coil of an implantable medical device that is implanted within tissue of a patient. For example, referring to FIG. 2, the external charging device 202 may apply the signal 224 to the primary coil 222 to cause the primary coil 222 to inductively couple to the secondary coil 242 of the implantable medical device 206. The method 600 also includes measuring a current at the primary coil, at 604. For example, referring to FIG. 2, the current measurement device 216 may measure the primary current. The measured current and other information, such as an induced voltage at the secondary coil, a duty cycle of the signal, etc. may be stored in a memory of the external charging device.

The method 600 further includes estimating a depth of the implantable medical device within the tissue of the patient based on the measured current (and other information, such as a dimension of the primary coil, a dimension of the secondary coil, the induced voltage at the secondary coil, or a combination thereof), at 606. For example, referring to FIG. 2, based on received voltage information and the measured primary current, the external charging device 202 may estimate a distance between the external charging device 202 and the implantable medical device 206. In a particular embodiment, the distance is estimated further based on a dimension of the primary coil 222, the dimension of the secondary coil 242, other information, or a combination thereof. The method 600 further includes determining whether the estimated depth is greater than a threshold depth, at 608. For example, referring to FIG. 2, the external charging device 202 may compare the estimated implant depth to a threshold depth.

The method 600 further includes notifying an operator that a recharge cycle may be extended to avoid overheating when the estimated depth is greater than the threshold depth, at 610. For example, referring to FIG. 2, when the estimated implant depth is greater than the threshold depth, the external charging device 202 may transmit a notification signal to the computing device 208 to notify the operator that a charging cycle may be extended to reduce and/or avoid overheating.

The method 600 further includes increasing a distance between the primary coil and the secondary coil when the estimated depth is less than the threshold depth, at 612. For example, referring to FIG. 2, when the estimated implant depth is less than the threshold depth, the external charging device 202 may transmit a notification signal to the computing device 208 to notify an operator (e.g., via a display) to increase the distance between the primary coil 222 and the secondary coil 242. In another example, the depth adjustment device 214 of FIG. 2 may be actuated to automatically increase the distance between the primary coil 222 and the secondary coil 242. In a particular embodiment, the method 600 further includes notifying an operator to apply a tissue simulation layer to skin of the patient, at 614. The tissue simulation layer has impedance that is substantially similar to impedance of human tissue. For example, referring to FIG. 2, the external charging device 202 may transmit a notification signal to the computing device 208 to notify an operator (e.g., via a display) to apply a tissue simulation layer 260 to the tissue surface 258.

Figure 7:
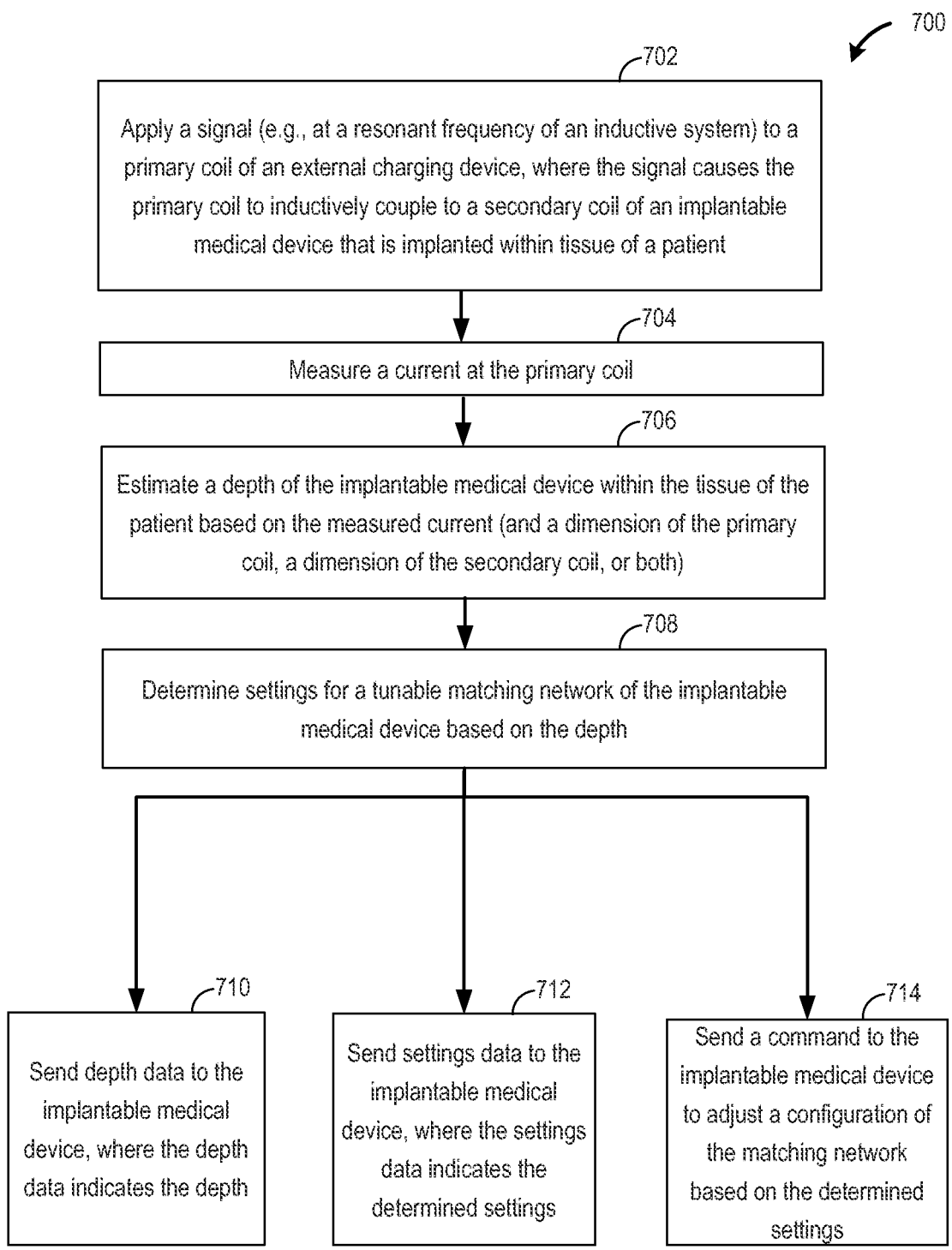
FIG. 7 is a flow chart of a second particular embodiment of a method of operation of the external charging device.

FIG. 7 is a flow chart of a second particular embodiment of a method 700 of operation of the external charging device, such as the external charging device 122 of FIG. 1 or the external charging device 202 of FIG. 2. The method 700 includes applying a signal (e.g., at a resonant frequency of an inductive system) to a primary coil of an external charging device, at 702. The signal causes the primary coil to inductively couple to a secondary coil of an implantable medical device that is implanted within tissue of a patient. For example, referring to FIG. 2, the external charging device 202 may apply one or more charging signals, such as the signal 224, to the primary coil 222 to cause the primary coil 222 to inductively couple to the secondary coil 242 of the implantable medical device 206. The method 700 also includes measuring a current at the primary coil, at 704. For example, referring to FIG. 2, the current measurement device 216 may measure the primary current corresponding to each of the charging signals.

The method 700 further includes estimating a depth of the implantable medical device within the tissue of the patient based on the measured current (as well as other information, such as a dimension of the primary coil, a dimension of the secondary coil, an induced voltage on the secondary coil, or a combination thereof), at 706. For example, referring to FIG. 2, based on voltage information received from the implantable medical device 206 and the one or more measured primary currents, the external charging device 202 may estimate a distance between the external charging device 202 and the implantable medical device 206.

The method 700 may include determining settings for a tunable matching network of the implantable medical device based on the depth, at 708. For example, referring to FIG. 2, the external charging device 202 may determine settings for the tunable matching network 248 based on the estimated implant depth and may transmit the determined setting to the implantable medical device 206 to tune the tunable matching network 248.

In a particular embodiment, the method 700 may include sending depth data to the implantable medical device, at 710. The depth data indicates the implant depth of the implantable medical device. For example, referring to FIG. 2, the external charging device 202 may transmit the estimated implant depth, as the depth data, to the implantable medical device 206. In a particular embodiment, the method 700 may include sending settings data to the implantable medical device, at 712. The settings data indicates settings for use by the implantable medical device 206, the external charging device 202, or both. For example, referring to FIG. 2, the external charging device 202 may transmit the determined settings as settings data to the implantable medical device 206. In a particular embodiment, the method 700 may include sending a command to the implantable medical device to adjust a configuration of the matching network based on the determined settings, at 714. For example, referring to FIG. 2, the external charging device 202 may transmit a command to the implantable medical device 206 to adjust a configuration of the tunable matching network 248 (e.g., impedance of the tunable matching network 248) based on the determined settings.

Although the description above contains many specificities, these specificities are utilized to illustrate some of the exemplary embodiments of this disclosure and should not be construed as limiting the scope of the disclosure. The scope of this disclosure should be determined by the claims, their legal equivalents and the fact that it fully encompasses other embodiments which may become apparent to those skilled in the art. A method or device does not have to address each and every problem to be encompassed by the present disclosure. All structural, chemical and functional equivalents to the elements of the disclosure that are known to those of ordinary skill in the art are expressly incorporated herein by reference and are intended to be encompassed by the present claims. A reference to an element in the singular is not intended to mean one and only one, unless explicitly so stated, but rather it should be construed to mean at least one. No claim element herein is to be construed under the provisions of 35 U.S.C. §112, sixth paragraph, unless the element is expressly recited using the phrase "means for." Furthermore, no element, component or method step in the present disclosure is intended to be dedicated to the public, regardless of whether the element, component or method step is explicitly recited in the claims.

The disclosure is described above with reference to drawings. These drawings illustrate certain details of specific embodiments that implement the systems and methods of the present disclosure. However, describing the disclosure with drawings should not be construed as imposing on the disclosure any limitations that may be present in the drawings. The present disclosure contemplates methods, systems and program products on any machine-readable media for accomplishing its operations. The embodiments of the present disclosure may be implemented using an existing computer processor, or by a special purpose computer processor incorporated for this or another purpose or by a hardwired system.

As noted above, embodiments within the scope of the present disclosure include program products comprising computer readable storage device, or machine-readable media for carrying, or having machine-executable instructions or data structures stored thereon. Such machine-readable media can be any available media which can be accessed by a general purpose or special purpose computer or other machine with a processor. By way of example, such machine-readable media can comprise RAM, ROM, EPROM, EEPROM, CD ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. The disclosure may be utilized in a non-transitory media. When information is transferred or provided over a network or another communications connection (either hardwired, wireless, or a combination of hardwired or wireless) to a machine, the machine properly views the connection as a machine-readable medium. Thus, any such a connection is properly termed a machine-readable medium. Combinations of the above are also included within the scope of machine-readable media. Machine-executable instructions comprise, for example, instructions and data which cause a general purpose computer, special purpose computer, or special purpose processing machines to perform a certain function or group of functions.

Embodiments of the disclosure are described in the general context of method steps which may be implemented in one embodiment by a program product including machine-executable instructions, such as program code, for example, in the form of program modules executed by machines in networked environments. Generally, program modules include routines, programs, objects, components, data structures, etc., that perform particular tasks or implement particular abstract data types. Machine-executable instructions, associated data structures, and modules represent examples of program code for executing steps of the methods disclosed herein. The particular sequence of such executable instructions or associated data structures represent examples of corresponding acts for implementing the functions described in such steps.

Embodiments of the present disclosure may be practiced in a networked environment using logical connections to one or more remote computers having processors. Logical connections may include a local area network (LAN) and a wide area network (WAN) that are presented here by way of example and not limitation. Such networking environments are commonplace in office-wide or enterprise-wide computer networks, intranets and the Internet and may use a wide variety of different communication protocols. Those skilled in the art will appreciate that such network computing environments will typically encompass many types of computer system configurations, including personal computers, hand-held devices, multi-processor systems, microprocessor-based or programmable consumer electronics, network PCs, servers, minicomputers, mainframe computers, and the like. Embodiments of the disclosure may also be practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

An exemplary system for implementing the overall system or portions of the disclosure might include a general purpose computing device in the form of a computer, including a processing unit, a system memory, and a system bus that couples various system components including the system memory to the processing unit. The system memory may include read only memory (ROM) and random access memory (RAM). The computer may also include a magnetic hard disk drive for reading from and writing to a magnetic hard disk, a magnetic disk drive for reading from or writing to a removable magnetic disk, and an optical disk drive for reading from or writing to a removable optical disk such as a CD ROM or other optical media. The drives and their associated machine-readable media provide nonvolatile storage of machine-executable instructions, data structures, program modules, and other data for the computer.

It should be noted that although the flowcharts provided herein show a specific order of method steps, it is understood that the order of these steps may differ from what is depicted. Also two or more steps may be performed concurrently or with partial concurrence. Such variation will depend on the software and hardware systems chosen and on designer choice. It is understood that all such variations are within the scope of the disclosure. Likewise, software and web implementations of the present disclosure could be accomplished with standard programming techniques with rule based logic and other logic to accomplish the various database searching steps, correlation steps, comparison steps and decision steps. It should also be noted that the word "component" as used herein and in the claims is intended to encompass implementations using one or more lines of software code, and/or hardware implementations, and/or equipment for receiving manual inputs.

The foregoing descriptions of embodiments of the disclosure have been presented for purposes of illustration and description. It is not intended to be exhaustive or to limit the disclosure to the precise form disclosed, and modifications and variations are possible in light of the above teachings or may be acquired from practice of the disclosure. The embodiments were chosen and described in order to explain the principals of the disclosure and its practical application to enable one skilled in the art to utilize the disclosure in various embodiments and with various modifications as are suited to the particular use contemplated.

The illustrations of the embodiments described herein are intended to provide a general understanding of the structure of the various embodiments. The illustrations are not intended to serve as a complete description of all of the elements and features of apparatus and systems that utilize the structures or methods described herein. Many other embodiments may be apparent to those of skill in the art upon reviewing the disclosure. Other embodiments may be utilized and derived from the disclosure, such that structural and logical substitutions and changes may be made without departing from the scope of the disclosure. For example, method steps may be performed in a different order than is shown in the figures or one or more method steps may be omitted. Accordingly, the disclosure and the figures are to be regarded as illustrative rather than restrictive.

Moreover, although specific embodiments have been illustrated and described herein, it should be appreciated that any subsequent arrangement designed to achieve the same or similar results may be substituted for the specific embodiments shown. This disclosure is intended to cover any and all subsequent adaptations or variations of various embodiments. Combinations of the above embodiments, and other embodiments not specifically described herein, will be apparent to those of skill in the art upon reviewing the description.

The Abstract of the Disclosure is submitted with the understanding that it will not be used to interpret or limit the scope or meaning of the claims. In addition, in the foregoing Detailed Description, various features may be grouped together or described in a single embodiment for the purpose of streamlining the disclosure. This disclosure is not to be interpreted as reflecting an intention that the claimed embodiments require more features than are expressly recited in each claim. Rather, as the following claims reflect, the claimed subject matter may be directed to less than all of the features of any of the disclosed embodiments.

What is claimed is:

1. A method comprising:
   applying a signal to a primary coil of an external charging device, wherein the signal causes the primary coil to inductively couple to a secondary coil of an implantable medical device that is implanted within tissue of a patient;
   measuring a current at the primary coil;
   estimating a depth of the implantable medical device within the tissue of the patient based on the measured current; and
   causing a configuration of a matching network of the implantable medical device to be adjusted by a processor in the implantable medical device, based on the depth.

2. The method of claim 1, wherein the signal is applied at a frequency that corresponds to a resonant frequency of an inductive system including the primary coil and the secondary coil.

3. The method of claim 1, further comprising, when the depth is estimated to be greater than a threshold depth, notifying an operator that a charging cycle may be extended.

4. The method of claim 1, further comprising, when the depth is estimated to be less than a threshold depth, increasing a distance between the primary coil and the secondary coil.

5. The method of claim 4, wherein the threshold depth corresponds to a designed implant depth of the implantable medical device.

6. The method of claim 1, further comprising determining settings for the matching network of the implantable medical device based on the depth.

7. The method of claim 1, wherein causing the configuration of the matching network of the implantable medical device to be adjusted includes sending depth data to the implantable medical device, wherein the depth data indicates the depth, and wherein the implantable medical device receives the depth data and adjusts the configuration of the matching network of the implantable medical device based on the depth data.

8. The method of claim 1, wherein the current at the primary coil is measured multiple times during a first charging period and wherein a lowest current value measured during the first charging period is used to estimate the depth.

9. The method of claim 1, wherein the matching network is adjusted during a charging period and prior to a communication period.

10. The method of claim 1, further comprising:
    receiving charging information determined during charging of the implantable medical device; and
    adjusting charging parameters based on the charging information.

11. A device comprising:
    a primary coil to inductively couple to a secondary coil of an implantable medical device;
    a current measurement device coupled to the primary coil that measures a current applied to the primary coil while the secondary coil is inductively coupled to the primary coil;
    a processor coupled to the current measurement device, the processor programmed to:
      estimate a depth of the implantable medical device within tissue of a patient based on the measured current; and
      cause settings for a matching network of the implantable medical device to be adjusted based on the depth.

12. The device of claim 11, wherein the primary coil inductively couples to the secondary coil in response to a signal applied to the primary coil while the primary coil is in proximity to the secondary coil, and wherein the signal is applied at a frequency that corresponds to a resonant frequency of an inductive system including the primary coil and the secondary coil.

13. The device of claim 11, further comprising a user interface device to provide a notification to an operator that a charging cycle may be extended when the depth is estimated to be greater than a threshold depth.

14. The device of claim 11, further comprising a depth adjustment apparatus that is movable to adjust a distance between the primary coil and the secondary coil.

15. The device of claim 11, further comprising a transmitter responsive to the processor that sends depth data to a receiver of the implantable medical device, wherein the depth data indicates the depth, and wherein the implantable medical device adjusts a configuration of the matching network of the implantable medical device based on the depth data.

16. The device of claim 11, wherein the current measurement device measures the current at the primary coil multiple times during a first charging period and wherein the processor estimates the depth based on a lowest current value measured during the first charging period.

17. The device of claim 11, further comprising a receiver that receives information from the implantable medical device indicating that a configuration of the matching network has been adjusted.

18. The device of claim 11, further comprising a receiver that receives from the implantable medical device configuration information regarding the matching network of the implantable medical device.

19. The device of claim 18, wherein the processor is further programmed to determine a type of tissue in which the implantable medical device is implanted based on the configuration information.

20. An implantable medical device comprising:
    a secondary coil to inductively couple to a primary coil of a second device;
    a receiver to receive depth data from the second device, wherein the depth data indicates a depth of the implantable medical device within tissue of a patient;
    a matching network coupled to the receiver; and
    a processor coupled to the matching network programmed to adjust a configuration of the matching network based on the depth data.

* * * * *